Figure 1:
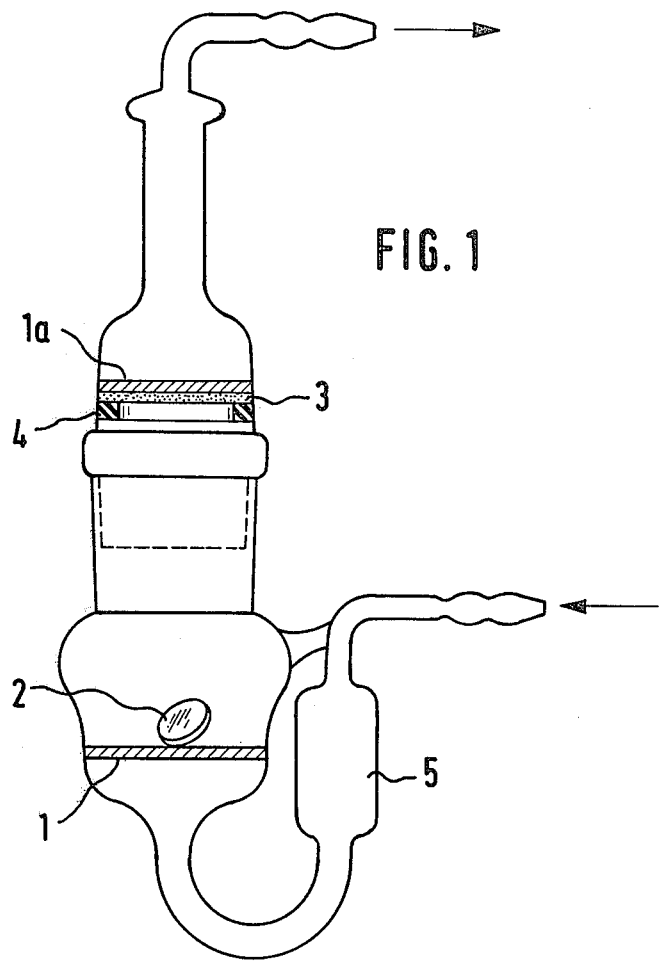

United States Patent [19]

Dahlhausen et al.

[11] 4,324,779
[45] Apr. 13, 1982

[54] METHOD FOR TREATING HYPERTONIA WITH N-(2-FURFURYL)-4-CHLORO-5-SULFAMOYL-ANTHRANILIC ACID AND PREPARATIONS THEREOF

[75] Inventors: Gebhard Dahlhausen, Kronberg; Hans-Werner Dibbern; Fülberth, both of Kelkheim; Gerhard Ross, Kriftel, all of Fed. Rep. of Germany

[73] Assignee: Hoechst Aktiengesellschaft, Frankfurt am Main, Fed. Rep. of Germany

[21] Appl. No.: 77,181

[22] Filed: Sep. 20, 1979

Related U.S. Application Data

[63] Continuation of Ser. No. 749,993, Dec. 13, 1976, abandoned, which is a continuation-in-part of Ser. No. 650,594, Jan. 20, 1976, abandoned, which is a continuation of Ser. No. 500,285, Aug. 26, 1974, abandoned.

[30] Foreign Application Priority Data

Aug. 28, 1973 [DE] Fed. Rep. of Germany ....... 2343218

[51] Int. Cl.³ .......................... A61K 9/22; A61K 9/32
[52] U.S. Cl. ...................................... 424/20; 424/32; 424/33
[58] Field of Search .................................. 424/16–38, 424/228, 229

[56] References Cited

U.S. PATENT DOCUMENTS

| | | | |
|---|---|---|---|
| 3,058,882 | 10/1962 | Sturm et al. | 424/228 |
| 3,361,632 | 1/1968 | Ross et al. | 424/22 |
| 3,456,049 | 7/1969 | Hotko et al. | 424/22 |
| 3,835,221 | 9/1974 | Fulberth et al. | 424/22 |
| 3,857,933 | 12/1974 | Ross et al. | 424/22 |

OTHER PUBLICATIONS

Davis et al. Current Medical Research & Opinion 5(9): 739–742 (1978) Diuretic Effect Of A Combined Preparation of Frusemide and Slow-Release Potassium Chloride.
PDR–1979 33rd Ed. Physicians' Desk Reference, pp. 915–917, "Lasix" (Furosemide).
Merck Index 9th Ed. 1976, entry 4161, "Furosemide" 8th Ed. (1968), p. 477 (Furosemide).
Halebian et al. J. Pharm. Sci. 58(8), 911–929, Aug. 1969, Pharmaceutical Applications of Polymorphism.
Finchor, J. Pharm. Sci. 57(11), 1825–1835, Nov. 1968, Particle Size of Drugs And Its Relationship To Absorption And Activity.
A.M.A. Drug Evaluations 2nd Ed. (1973), pp. 45, 50, 73, 74, 197, 199.
Dibbern et al. Pharmazeutische Zeitung 48: 1848–1853, Dec. 2, 1971, English Translation.

*Primary Examiner*—Shep K. Rose
*Attorney, Agent, or Firm*—Curtis, Morris & Safford

[57] ABSTRACT

A method for treating hypertonia with a preparation of N-(2-furfuryl)-4-chloro-5-sulfamoyl-anthranilic acid having a slightly retarded release, wherein the release of the active substance in vitro, measured in the flow through-cell to Dibbern, is not more than 5% after 1 hour in a buffer solution of pH 1.5 and about 10 to at most 25% of the active substance content after a two-hour treatment in a buffer solution of pH 5.5.

1 Claim, 4 Drawing Figures

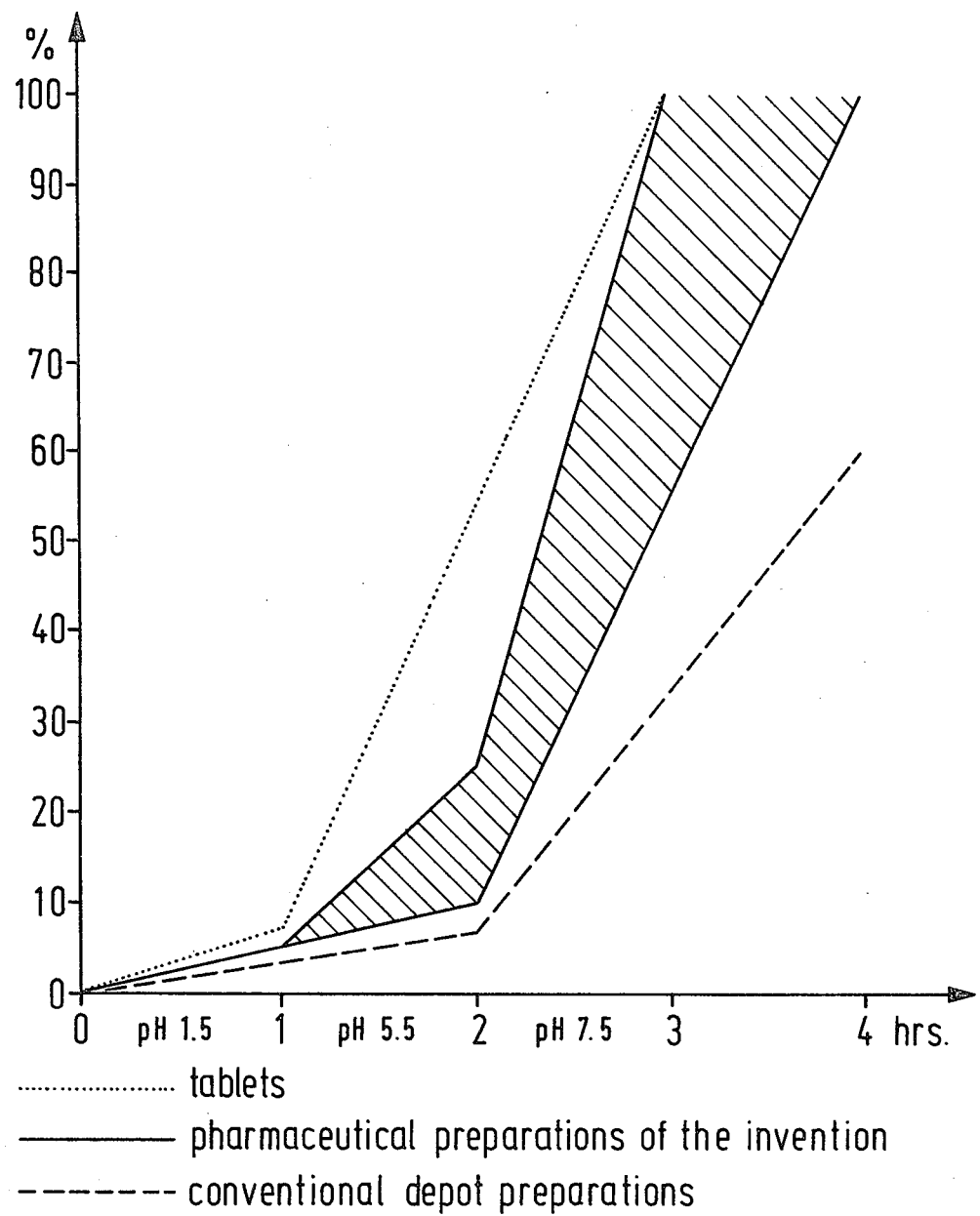

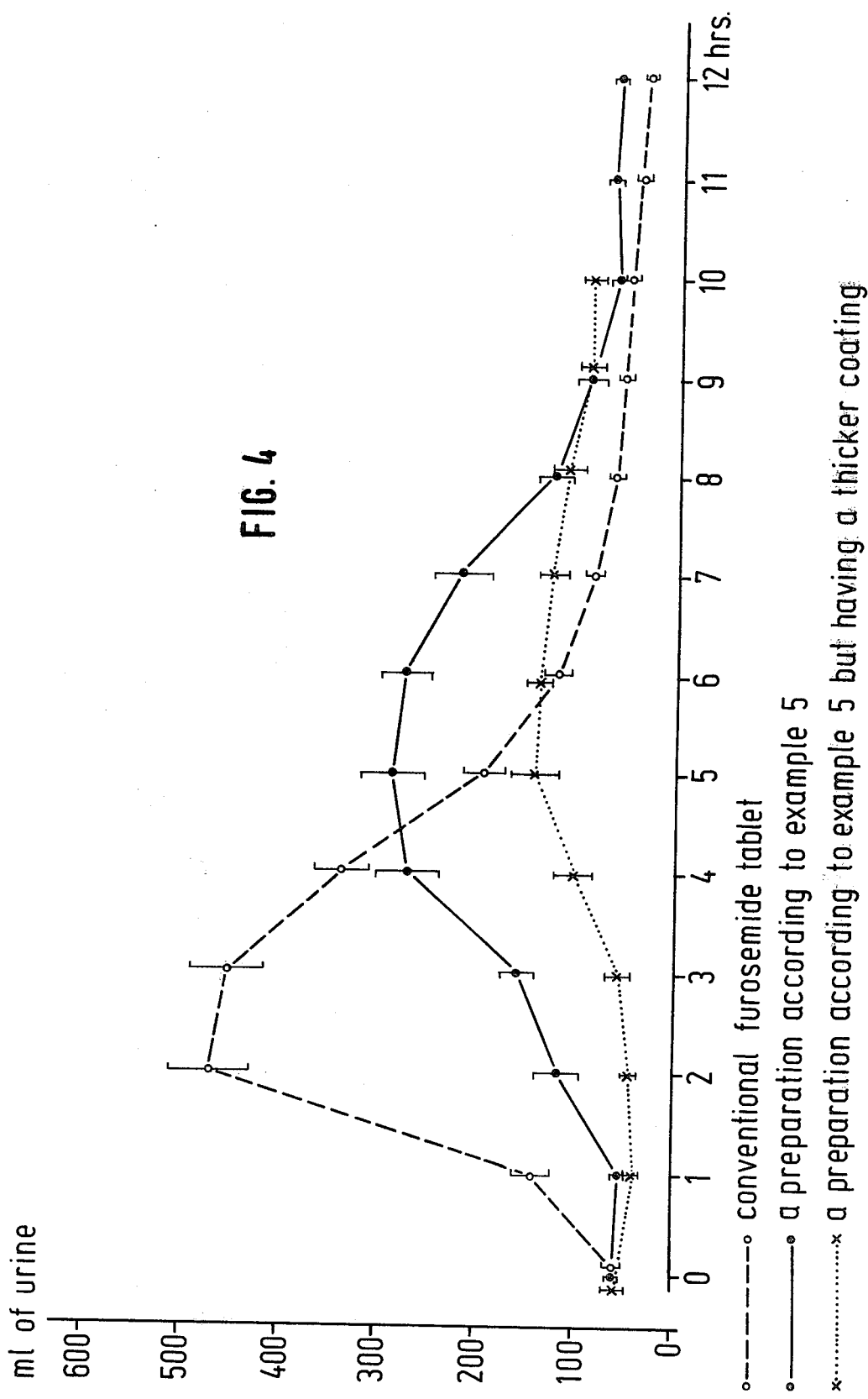

METHOD FOR TREATING HYPERTONIA WITH N-(2-FURFURYL)-4-CHLORO-5-SULFAMOYL-ANTHRANILIC ACID AND PREPARATIONS THEREOF

This is a continuation of pending application Ser. No. 749,993 filed Dec. 13, 1976, now abandoned, which is in turn a continuation-in-part of application Ser. No. 650,594 filed Jan. 20, 1976 and now abandoned, which is in turn a continuation of application Ser. No. 500,285 filed Aug. 26, 1974 and now abandoned.

The present invention relates to a method for treating hypertonia with preparations containing N-(2-furfuryl)-4-chloro-5-sulfamoyl-anthranilic acid and to such preparations.

The salidiuretic furosemide, N-(2-furfuryl)-4-chloro-5-sulfamoyl-anthranilic acid of the formula

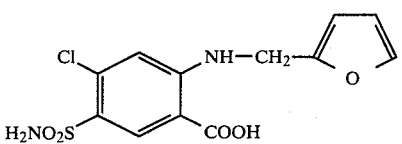

administered per os to human patients brings about a substantial increase in diuresis already within the first hour after administration, the effect continuing for some hours and then wearing off rapidly. The rapid onset of the diuretic effect demonstrates an immediate absorption of these diuretics after administration in the gastrointestinal tract.

In the treatment of hypertonia, diuretics are used in combination with other hypotonic agents, such as Reserpin, α-methyl-DOPA and others. Since a treatment with those combined preparations has often to be carried out over several months, the rapid onset of the effect of furosemide immediately after administration always means intensified diuresis to the patient. It is therefore desirable to modify the activity of furosemide by means of a suitable preparation which prevents an undesired diuresis peak in the treatment of hypertonia immediately after administration of the medicament by levelling it out over a prolonged period of time.

A reproducible and safe treatment of hypertonia cannot be achieved using medicinal forms suitable for conventional preparations of retarded effect having a sustained release of the active substance over up to 12 hours.

It is known to prepare diuretics having a retarded effect by means of conventional galenic methods, such as enveloping them with coatings which are soluble at various pH-values but are resistant at acid pH-values. In the case of such furosemide preparations, however, the times at which diuresis occurs differ greatly over a period of about 10 hours.

This invention now relates to a method for treating hypertonia using novel furosemide preparations having a slightly retarded release, wherein the release of active substance in vitro, measured in the "flow-through-cell", according to Dibbern, is not more than 5% after 1 hour in a buffer solution of pH 1.5 and about 10 to at most 25% after a two-hour treatment in a buffer solution of pH 5.5.

The flow-cell according to Dibbern corresponds to FIG. 1 and consists of lower and upper part connected by a normal ground joint. Both parts are fitted with a sintered frit 1 and 1a, diameter 20 mm, either as support for the sample 2 to be examined (lower part), or as a filter medium in the upper part.

The filter medium is delivered in the form of a 20 mm diameter round filter 3 of an approved material. The filter is situated in the upper part of the cell, before the sinter, and is fixed with a rubber ring 4. The enlarging tube which is connected in series to the lower part serves as bubble trap 5 (c.f. "Pharmazeutische Zeitung", vol. 116, (1971) pages 1848–1853).

Figure 2:
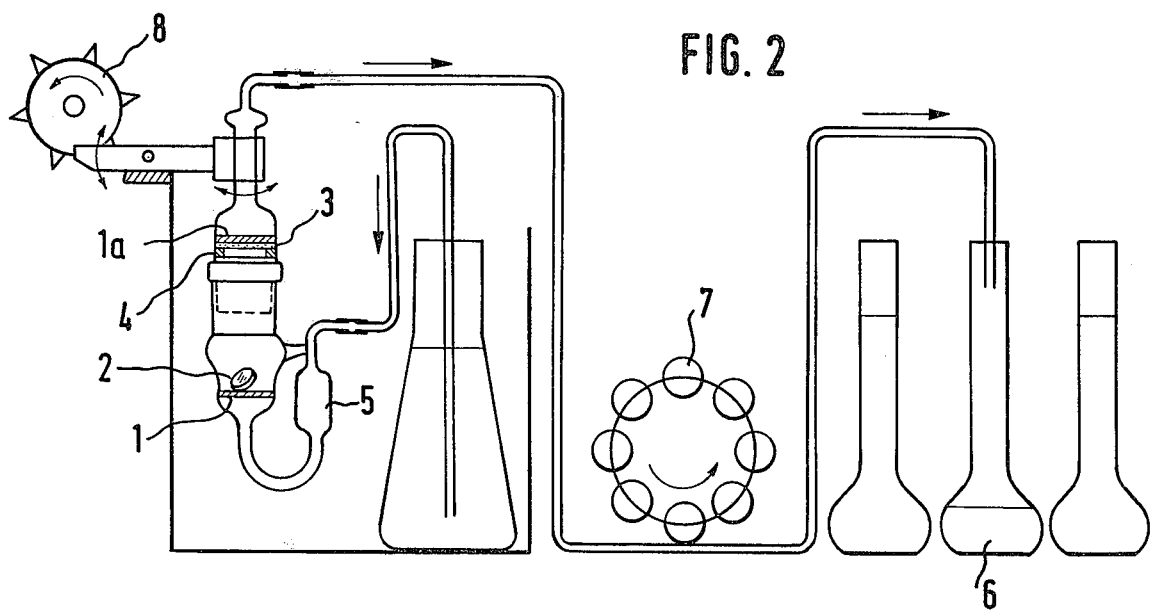

The flow-cell used in the tests is this one known as Desaga Flowcell 14 70 60 (C. Desaga GmbH, 6900 Heidelberg), the grouping of the cell and the other instruments such a collecting flask 6, peristaltic pump 7 and device 8 for pendulum movement of the flow cell is shown in FIG. 2. The release of the active ingredient is measured in the cell without backflow in order to have a good separation of the different pH-values. A number of fractions is collected and the concentration of the dissolved active substance is determined. The rate of flow of the solvent is 100 ml per hour.

The buffer solution of pH 1.5 is a mixture of 3.38 parts by volume of an aqueous solution containing per liter 7.507 g of amino acetic acid and 5.84 g of sodium chloride and 66.2 parts by volume of 0.1 n hydrochloric acid. To this mixture there is added 0.01% of polyoxyethylene-sorbitane oleate.

The second buffer solution, which is used in the tests, is a mixture of 3.9 parts of an 1/15 m disodium-hydrogen phosphate solution and of 96.1 parts of an 1/15 m potassium-dihydrogen phosphate solution to which there is added 0.01% of polyoxyethylene-sorbitane oleate.

In order to have in the in-vitro tests similar conditions as in vivo, the measurements are made with pendulum movement and the temperature in the whole system is 37° C.

These furosemide preparations can be manufactured by formulating furosemide into a dosage unit form from which the release of the active substance from the preparation in vitro, measured in the flow-through-cell according to Dibbern, is not more than 5% after 1 hour in a buffer solution of pH 1.5 and about 10 to at most 25% after a two-hour treatment in a buffer solution of pH 5.5, by applying galenic methods of manufacture known per se [see, for example, the periodical "Pharma International" (1971), page 18 et seq.] to furosemide.

The low release according to the invention is extremely surprising. As shown in the attached FIG. 3 conventional medicinal forms, for example rapidly disintegrating tablets which release 40 to 50% at pH 5.5, exceed by far this value of 20% within the second hour after administration, thus rapidly reaching a diuresis peak. It has been found in in-vivo tests that only those preparations showed the optimum retarded effect of furosemide the release of active substance of which took place in vitro in the claimed release range. Pharmaceutical preparations that have a more rapid release of active substance in vitro, led to the above described undesired diuresis peak. The preparations with slower release of the active substance in vitro, however, produced too small a diuresis and, therefore, essentially reduced the effect of furosemide.

Medicinal forms, for example preparations which are extremely soluble in the small intestine or preparations which release the active substance very slowly, show release values less than 10% at pH 5.5 within the second hour of examination, thus substantially reducing the overall amount of the active substance of the medicament totally absorbed. The preparations of the invention release the active substance almost entirely within 3 to 4 hours.

It is evident from the attached FIG. 4 which shows the rate of diuresis after oral administration of 60 mg furosemide that after the administration of furosemide tablets to human beings the diuresis peak is reached within two hours. This is in accordance with the fact observed in the flowcell; the main part of furosemide is released within two hours. The FIG. 4 shows furthermore that 2 hours after the oral administration of a preparation according to example 5 of the present application only about 25% of the whole diuresis rate is reached. The highest level of the diuresis is reached 4 to 5 hours after the administration. The diuresis rate is within the desired range and in accordance with the release rate observed in the flowcell. Finally the FIG. 4 shows the slow diuresis rate after the oral administration of a preparation with sustained release which differs from this one of example 5 by a thicker coating consisting of 30 to 35 layers.

All the facts observed in the in-vivo-tests are in accordance with these observed in the flowcell according to Dibbern. Therefore a preparation showing the desired release rate of the active substance as measured in the Dibbern flowcell is suitable for the treatment of hypertonia.

As medicinal forms containing furosemide, which are especially convenient for the treatment of hypertonia, any orally administrable medicament with a precisely controlled release is suitable.

According to the preferable embodiment of this invention, appropriate preparation forms, from which furosemide is released in the precisely controlled manner mentioned above, is manufactured by formulating furosemide in the final preparation form having the above mentioned release properties of the active substance by means of (a) preparing active substance crystals having a special particle size fraction (so called macro crystals), or providing active substance crystals with coatings that retard solubility (e.g. micro capsules); or (b) providing mono- or multi layer shaped preparations of the active substance with a special coating, which start disintegrating in a weakly acid pH-value; or (c) adding lipophilic fats, plastics and/or waxes or hydrophilic swelling agent or surface-active substance to the active substance; or (d) binding the active substance to ion exchanger or in complexed form; or (e) preparing gelating depot capsules which release their active substance in protracted form from the porous matrix after solidification of the contents in the gastro-intestinal tract, in a known manner per se.

Even a combination of the measures known per se and either one method mentioned sub (a) to (e) fall within the scope of this invention, provided the release of active substance according to the invention, measurable in the flow-through-cell according to Dibbern, is reached by suitably adapting the methods concerned.

In the method (a), the range of the suitable crystal size is between 0.3 and 0.5 mm. Such furosemide macro crystals are prepared, for example, according to the following procedure:

An almost saturated solution is prepared by dissolving 10.0 parts by weight of finely powdered furosemide in 185 parts by volume of boiling ethanol. The resulting clear solution is diluted by adding 60 parts by volume of 40% by volume boiling ethanol. This solution is allowed to cool very slowly in an almost tightly sealed vessel (for example by placing it in a heating cabinet which has been heated to 75° C. and then energy has been cut). After room temperature has been reached, the solution can slowly be cooled to about 8° C.

The crystals which have separated from the solution are suction filtered by means of a filter frit and washed with a small amount ice-cold ethanol. In this manner, crystals are obtained which have a size of about 150 to 500 microns (0.15 to 0.5 mm). The desired particle size fraction (i.e. 0.3 to 0.5 mm) are obtained by sieving the crystals, where required crushing them carefully and sieving them once more.

In the method (b), special coatings which start disintegrating already at a weakly acid pH-value are applied to the active substance in medicinal form to modify the release of their active ingredient. The application of such special coatings is carried out by using many, indeed equivalent galenic methods known per se.

Examples of those substances useful as retarding coating are laquers which are soluble in the small intestine, such as cellulose acetate, phthalate, hydroxy-propyl-methyl cellulose phthalate, acrylates, shellac or cellulose derivatives, such as methyl cellulose, ethyl cellulose fats, fatty acid derivatives, waxes, polyvinyl pyrrolidone, swelling agents and so on.

The in-vivo test results show that the medicinal form of coated pellets as mentioned in Example 5 hereinafter is most promising galenic variant of the furosemide retard preparations of this invention.

The coating may be applied to mecidicinal forms of furosemide as mono layer, and preferably as multi layer. When the coating is applied as multi layer, the optimum range of the number of layers depend on the compositions of the coatings, and in the case of the coating as described in Example 5, the optimum range is 15 to 25 layers.

According to the method (c) of this invention, for retarding the active ingredient release from the solid oral preparations, the following substances are used together with the adjuvants to make tablets or filling capsules (as in Example 4) as mixing constituents in the indicated concentrations:

| | |
|---|---|
| Polyglycol 4.000 | 5–15% |
| Polyvinyl pyrrolidone K 25 | 5–15% |
| Hoechst Wachs E$^{(R)}$ | 10–20% |
| (wax acid-polyglycol ester) | |
| Carbopol 934$^{(R)}$ | 8–15% |
| (polyacrylate) | |
| bees-wax | 10–20% |
| hydrogenated castor oil | 5–15% |

Used on an average of the amounts indicated, the above substances afforded an in-vitro release of the active ingredient within the range defined above. Thus, there is obtained the drugs which have sustained disintegration or controlled release of active ingredient.

Other adjuvants suitable for the preparation according to this invention are, for example, polyethylene, polyvinyl chloride, polyethylene glycol of other polymerization degrees, fatty acid esters, fatty alcohols, synthetic and natural waxes, paraffins, fatty acid amides, polyacrylate compounds, alginic acid and derivatives thereof; cellulose derivatives, casein, silicones, shellac, copolymers of vinyl polymers with maleic anhydride, vegetable swelling agents, gelating and the like.

Furthermore, according to the process of this invention, furosemide may be bound to a suitable ion-exchanger such as ion exchangers on polyacrylate basis having tertiary amine or quaternary ammonium groups, for example, Dowex 2×8 ®, Amberlite IRA 68 ®, Amberlyst A 21 Amberlyst A 26 or may be reacted with a suitable complex-forming compound and thus, there can be obtained the preparation which release of the active ingredient is controlled.

According to still another embodiment of this invention [method (e)], capsules having special coatings or capsules having walls of which solubility has been modified to be adapted so as to have the release patern of the active ingredient defined herein before is provided. The compositions of such special coatings or walls may be the same as already described in method (b).

The gelatin depot capsules manufactured by this method (e) disperse readily their walls in the digestive fluid, e.g. the gastro-intestinal tract, and then their release of active ingredient from the porous matrix is protracted after solidification of their contents. That is, the contents of the capsules forms a consistent gel (jelly) which includes the active substance as a matrix, when they come into contact with water or the acidic gastric juice. This matrix is degraded in the digestive tube only slowly with the release of the medicament being retarded.

An example of such medicinal form are Scherer's retard soft gelatin capsules containing, as adjuvant polyethylene, shellac and physiologically acceptable polyalcohols.

The following Examples illustrate the invention.

EXAMPLE 1

Furosemide macro crystals

Furosemide crystals were formed from 80% ethanol and screened by means of sieve fractionation to reach a particle size fraction of 0.3 to 0.4 mm.

These macro crystals were filled into hard gelatine capsules at a fill weight of 60 mg.

Release in vitro in the flow-through-cell according to Dibbern:

| after the first hour at pH 1.5: | 1% |
| after the second hour at pH 5.5: | 17% |

EXAMPLE 2

| Coated tablets containing a release retarding matrix | | |
|---|---|---|
| (A) Tablet cores | per core | for 100,000 cores |
| 1. Furosemide | 60.0 mg | 6.00 kg |
| 2. lactose | 53.0 mg | 5.30 kg |
| 3. microcrystalline cellulose | 15.0 mg | 1.50 kg |
| 4. ultra amylopectin | 5.0 mg | 0.50 kg |
| 5. finely dispersed silicic acid | 3.0 mg | 0.30 kg |
| 6. talcum | 2.0 mg | 0.20 kg |
| 7. hydrogenated castor oil | 25.0 mg | 2.50 kg |
| 8. ultra amylopectin | 10.0 mg | 1.00 kg |
| 9. talcum | 5.0 mg | 0.50 kg |
| 10. finely dispersed silicic acid | 1.0 mg | 0.10 kg |

| -continued | | |
|---|---|---|
| Coated tablets containing a release retarding matrix | | |
| (A) Tablet cores | per core | for 100,000 cores |
| 11. magnesium stearate | 1.0 mg | 0.10 kg |
| | 180.0 mg | 18.00 kg |

The substances 1 to 7 were homogeneously mixed and processed into granules having a particle size of 0.6 to 1.2 mm. In a roller mill, the outer phase 8 to 11 was evenly admixed to the granules 1 to 7.

The powdered granules were then compressed into biconvex tablets cores having a diameter of 8 mm and a final weight of 180 mg.

(B) Coating

Subsequently, a coating of sugar, gelatin, Arabic gum, calcium carbonate, dyes and gloss waxes was applied in known manner. Release in vitro in the flow-through-cell according to Dibbern:

| after the first hour at pH 1.5: | 1% |
| after the second hour at pH 5.5: | 12 to 17% |

EXAMPLE 3

Drop pills containing a release retarding matrix

Drop granules having a particle size of 0.3 to 0.6 mm were prepared from a melt of

| furosemide | 60.0 mg |
| polyoxy-ethylene sorbitane mono-oleate | 81.8 mg |
| glycol ester of a wax acid | 152.2 mg |
| | 294.0 mg | using a device according to German Offenlegungsschrift No. 1 918 685.

294 mg each of these pills were filled into hard gelatine capsules.

Release in vitro in the through-flow-cell according to Dibbern:

| after the first hour at pH 1.5: | 3.5% |
| after the second hour at pH 5.5: | 20.0% |

EXAMPLE 4

Furosemide tablets containing a release retarding matrix

| | per tablet | for 100,000 tablets |
|---|---|---|
| 1. Furosemide | 60.0 mg | 6.00 kg |
| 2. lactose | 84.0 mg | 8.40 kg |
| 3. cornstarch | 8.0 mg | 0.80 kg |
| 4. polyvinyl pyrrolidone K 25 | 15.0 mg | 1.50 kg |
| 5. talcum | 7.0 mg | 0.70 kg |
| 6. talcum | 5.0 mg | 0.50 kg |
| 7. magnesium stearate | 1.0 mg | 0.10 kg |
| | 180.0 mg | 18.00 kg |

The substances 1 to 5 were homogeneously mixed and processed into granules having a particle size of 0.6 to 1.2 mm. In a roller mill, the lubricants 6 and 7 are evenly admixed to the granules 1 to 5.

The powdered granules were compressed into biconvex tablets each having a diameter of 8 mm and a final weight of 180 mg. Release in vitro in the flow-through-cell according to Dibbern:

| after the first hour at pH 1.5: | 3.5% |
|---|---|
| after the second hour at 5.5: | 15 to 17% |

EXAMPLE 5

Coated pellets

1 Kilogram of homeopathic sugar pills having an average diameter of 1 mm were evenly wetted in a coating vessel with a 10% alcoholic solution of polyvinyl pyrrolidone K 25 as an adhesive, then 20 g of finely dispersed furosemide were added as a powder, the pills were covered with 10 g of talcum and dried with blast air.

The above-mentioned working method was repeated 10 times to apply about 200 g of furosemide substance.

1 Kilogram of these pellets having an active substance-containing coating was enveloped in 20 layers of a sealing coating made from

| shellac | 33.0 g |
|---|---|
| stearic acid | 67.0 g |
| ethyl alcohol | 700.0 ml and |
| methylene chloride | 300.0 ml | while drying each layer applied by means of blast air.

The coated pills were filled into hard gelatine capsules, each containing an active substance content of 60 mg of furosemide. Release in vitro in the flow-through-cell according to Dibbern:

| after the first hour at pH 1.5: | 1% |
|---|---|
| after the second hour at pH 5.5: | 9 to 10%. |

EXAMPLE 6

Coated pellets

1 Kilogram of homeopathic sugar pills having an average diameter of 0.7 to 0.9 mm were evenly wetted in a coating vessel with a 15% alcoholic solution of polyvinyl pyrrolidone K 25 as an adhesive, then 30 g of a mixture of equal parts of furosemide and talcum were added as a powder and dried with blast air.

The above mentioned working method was repeated 10 times to apply about 150 g of furosemide substance.

1 Kilogram of these pellets having an active substance containing coating was enveloped in a sealing coating made from

| polymethacrylic acid-dispersion | 700.0 g |
|---|---|
| titandioxide | 30.0 g |
| polyethylene glycol 600 | 5.0 g |
| water, free of minerals | 760.0 g |

The coating can be applied continuously or non-continuously. Normally 15 to 25 layers are applied.

The coated pills were filled into hard gelatine capsules each containing an active substance content of 60 mg of furosemide.

Release in vitro in the flow-through-cell according to Dibbern:

| after the first hour at pH 1.5: | 3% |
|---|---|
| after the second hour at pH 5.5: | 18% |

What is claimed is:

1. A furosemide-containing pellet for the oral administration of furosemide, said pellet consisting essentially of a core of furosemide having thereover a sustained-release coating which starts to dissolve in a weakly acid medium, which coating, when its release characteristics are measured in vitro in a flow-through-cell according to Dibbern,
   (a) releases not more than 5 percent of said furosemide into a buffer solution having a pH of 1.5 during the first hour of measurement in said cell;
   (b) releases about 10 to at most 25 percent of said furosemide into a buffer solution having a pH of 5.5 during the second hour of measurement in said cell; and
   (c) releases the remainder of said furosemide substantially completely into a buffer solution having a pH of 7.5 during the third and fourth hours of measurement in said cell.

* * * * *

UNITED STATES PATENT OFFICE
CERTIFICATE OF CORRECTION

Patent No. 4,324,779     Dated April 13, 1982

Inventor(s) Dahlhausen et al.

It is certified that error appears in the above-identified patent and that said Letters Patent are hereby corrected as shown below:

On the title page:

In the Heading [item 75], "Fülberth" should be --Werner Fülberth--;

In the Heading [item 63] and in Column 1, line 10, each occurrence of "650,594" should read --650,694--.

Signed and Sealed this

Nineteenth Day of April 1983

[SEAL]

Attest:

GERALD J. MOSSINGHOFF

Attesting Officer     Commissioner of Patents and Trademarks